United States Patent [19]

Shields

[11] 4,100,117

[45] Jul. 11, 1978

[54] SOMATOSTATIN ANALOGS AND INTERMEDIATES THERETO

[75] Inventor: James E. Shields, Indianapolis, Ind.

[73] Assignee: Eli Lilly and Company, Indianapolis, Ind.

[21] Appl. No.: 789,472

[22] Filed: Apr. 21, 1977

[51] Int. Cl.$^2$ .................. C08L 37/00; C07C 103/52; A61K 37/00

[52] U.S. Cl. ................................ 260/8; 260/112.5 S; 424/177

[58] Field of Search ............................ 260/112.5 S, 8; 424/177

[56] References Cited

PUBLICATIONS

L. Ferland et al., Chem. Abst., 85, 1976, p.72658y.

Primary Examiner—Delbert R. Phillips
Attorney, Agent, or Firm—William C. Martens, Jr.; Arthur R. Whale

[57] ABSTRACT

The tetradecapeptide

D-Val-Gly-L-Cys-L-Lys-L-Asn-L-Phe

-L-Phe-L-Trp-L-Lys-L-Thr-L-Phe-L-Thr-L-Ser-L-Cys-OH is described along with corresponding non-toxic pharmaceutically-acceptable acid addition salts as well as intermediates useful in the synthesis of the tetradecapeptide. This tetradecapeptide as well as its pharmaceutically-acceptable acid addition salts exhibit various activities including inhibition of the release of gastric acid and reduction of gut motility.

10 Claims, No Drawings

SOMATOSTATIN ANALOGS AND INTERMEDIATES THERETO

BACKGROUND AND SUMMARY OF THE INVENTION

This invention is directed to the tetradecapeptide

D-Val-Gly-L-Cys-L-Lys-L-Asn-L-Phe
            |_____
            -L-Phe-L-Trp-L-Lys-L-Thr-L-Phe-L-Thr-L-Ser-L-Cys-OH as well as to its pharmaceutically acceptable acid addition salts and to intermediates produced during the synthesis of the tetradecapeptide.

Somatostatin (also known as somatotropin release inhibiting factor) is a tetradecapeptide of the formula L-Ala-Gly-L-Cys-L-Lys-L-Asn-L-Phe-L-Phe-L-Trp-L-Lys-L-
            |_____
            Thr-L-Phe-L-Thr-L-Ser-L-Cys-OH.

This tetradecapeptide was isolated from ovine hypothalamic extracts and was found to be active in inhibiting the secretion of growth hormone (GH), also known as somatotropin. In this regard, see P. Brazeau, W. Vale, R. Burgus, N. Ling, M. Butcher, J. Rivier, and R. Guillemin, Science, 179, 77 (1973).

In addition, U.S. Pat. No. 3,904,594 discloses natural somatostatin as well as a generic class of other compounds having the dodecapeptide sequence represented by positions 3–14 of the natural hormone. Furthermore, the compound conveniently designated as D-Ala[1]-somatostatin was previously reported in Ferland et al., *Molecular and Cellular Endocrinology*, 4, 79–88 (1976).

The biologically active tetradecapeptide of this invention has the formula defined above and includes the non-toxic acid addition salts thereof. Its structure differs from that of somatostatin by the presence of a D-valine residue in position 1 in place of an L-alanine residue. For convenience sake, the tetradecapeptide of this invention can be referred to as D-Val[1]-somatostatin.

Thus, this invention is directed to a compound selected from those of the formula H-D-Val-Gly-L-Cys-L-Lys-L-Asn-L-Phe-L-Phe-L-Trp-L-Lys-L-Thr-L-Phe-L-Thr-L-Ser-L-Cys-OH and its pharmaceutically-acceptable non-toxic acid addition salts, and R-D-Val-Gly-L-Cys($R_1$)-L-Lys($R_2$)-L-Asn-L-Phe-L-Phe-L-Trp($R_5$)-L-Lys($R_2$)-L-Thr($R_3$)-L-Phe-L-Thr($R_3$)-L-Ser($R_4$)-L-Cys($R_1$)-X; in which R is hydrogen or an α-amino protecting group;
$R_1$ is hydrogen or a thio protecting group;
$R_2$ is hydrogen or an ε-amino protecting group;
$R_3$ and $R_4$ each are hydrogen or a hydroxy protecting group;
$R_5$ is hydrogen or formyl; and
X is hydroxy or

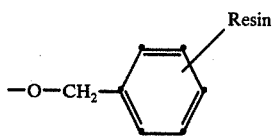

in which the resin is polystyrene; with the proviso that, when X is hydroxy, each of R, $R_1$, $R_2$, $R_3$, $R_4$, and $R_5$ is hydrogen, and, when X is

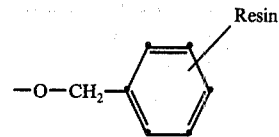

each of R, $R_1$, $R_2$, $R_3$, and $R_4$ is other than hydrogen.

DETAILED DESCRIPTION OF THE INVENTION

As indicated above, this invention in part is directed to a compound conveniently referred to as D-Val[1]-somatostatin, as well as to its pharmaceutically-acceptable non-toxic acid addition salts.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from acetic acid. Any of the above salts are prepared by conventional methods.

Also contemplated as being within the scope of this invention are intermediates of the formula R-D-Val-Gly-L-Cys($R_1$)-L-Lys($R_2$)-L-Asn-L-Phe-L-Phe-L-Trp($R_5$)-L-Lys($R_2$)-L-Thr($R_3$)-L-Phe-L-Thr($R_3$)-L-Ser($R_4$)-L-Cys($R_1$)-X.

Preferred intermediates include:

H-D-Val-Gly-L-Cys-L-Lys-L-Asn-L-Phe-L-Phe-L-Trp-L-Lys-L-Thr-L-Phe-L-Thr-L-Ser-L-Cys-OH; and N-(BOC)-D-Val-Gly-L-(PMB)Cys-L-(CBzOC)-Lys-L-Asn-L-Phe-L-Phe-L-(For)Trp-L-(CBzOC)-Lys-L-(Bzl)Thr-L-Phe-L-(Bzl)Thr-L-

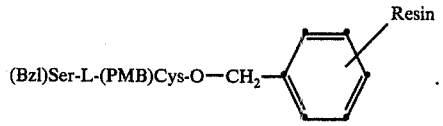

The above formulas defining the intermediates include protecting groups for amino, hydroxy, and thio (sulfhydryl) functions. The properties of a protecting group as defined herein are two-fold. First, the protecting group prevents a reactive moiety present on a particular molecule from undergoing reaction during subjection of the molecule to conditions which could cause disruption of the otherwise active moiety. Secondly, the protecting group is such as can be readily removed with restoration of the original active moiety and under conditions which would not undesirably affect other portions of the molecule. Groups which are useful for these purposes, that is, for protecting amino, hydroxy, and thio groups, are well recognized by those skilled in the art. Indeed, entire volumes have been directed specifically to a description and discussion of methods for using such groups. One such volume is the treatise Protective Groups in Organic Chemistry, M. F. W. McOmie, Editor, Plenum Press, New York, 1973.

In the above formulas defining the intermediates, R represents either an α-amino hydrogen or an α-amino protecting group. The α-amino protecting groups contemplated for R are well recognized by those of ordinary skill in the peptide art. Many of these are detailed in McOmie, supra, Chapter 2, authored by J. W. Barton. Illustrative of such protecting groups are benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-methoxybenzyloxycarbonyl, p-nitrobenzyloxycarbonyl, t-butyloxycarbonyl (BOC), t-amyloxycarbonyl, 2-(p-biphenyl)isopropyloxycarbonyl (BpOC), adamantyloxycarbonyl, isopropyloxycarbonyl, cyclopentyloxycarbonyl, cyclohexyloxycarbonyl, cycloheptyloxycarbonyl, triphenylmethyl (trityl), p-toluenesulfonyl, and the like. Preferably, the α-amino protecting group defined by R is t-butyloxycarbonyl.

$R_1$ represents either the hydrogen of the sulfhydryl group of the cysteine or a protecting group for the sulfhydryl substituent. Many such protecting groups are described in McOmie, supra, Chapter 7, authored by R. G. Hickey, V. R. Rao, and W. G. Rhodes. Illustrative suitable such protecting groups are p-methoxybenzyl, benzyl, p-tolyl, benzhydryl, acetamidomethyl, trityl, p-nitrobenzyl, t-butyl, isobutyloxymethyl, as well as any of a number of trityl derivatives. For additional groups, see, for example, Houben-Weyl, Methodes der Organischen Chemie, "Synthese von Peptiden," Vols. 15/1 and 15/2, (1974), Stuttgart, Germany. Preferably, the sulfhydryl protecting group defined by $R_1$ is p-methoxybenzyl.

$R_2$ represents either hydrogen on the ε-amino function of the lysine residue or a suitable ε-amino protecting group. Illustrative of such groups are the bulk of those mentioned hereinabove as being suitable for use as an α-amino protecting group. Included as typical such groups are benzyloxycarbonyl, t-butyloxycarbonyl, t-amyloxycarbonyl, cyclopentyloxycarbonyl, adamantyloxycarbonyl, p-methoxybenzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, isopropyloxycarbonyl, cyclohexyloxycarbonyl, cycloheptyloxycarbonyl, p-toluenesulfonyl, and the like.

As will become apparent hereinafter, the method of preparation of the tetradecapeptides of this invention involves periodic cleavage of the α-amino protecting group from the terminal amino acid present on the peptide chain. Thus, the only limitation with respect to the identity of the ε-amino protecting group on the lysine residue is that it be such that it will not be cleaved under the conditions employed to selectively cleave the α-amino protecting group. Appropriate selection of the α-amino and the ε-amino protecting groups is a matter well within the knowledge of a peptide chemist of ordinary skill in the art and depends upon the relative ease with which a particular protecting group can be cleaved. Thus, groups such as 2-(p-biphenylyl)-isopropyloxycarbonyl (BpOC) and trityl are very labile and can be cleaved even in the presence of mild acid. A moderately strong acid, such as hydrochloric acid, trifluoroacetic acid, or boron trifluoride in acetic acid, is required to cleave other groups such as t-butyloxycarbonyl, t-amyloxycarbonyl, adamantyloxycarbonyl, and p-methoxybenzyloxycarbonyl. Even stronger acid conditions are required to effect cleavage of other protecting groups such as benzyloxycarbonyl, halobenzyloxycarbonyl, p-nitrobenzyloxycarbonyl, cycloalkyloxycarbonyl, and isopropyloxycarbonyl. Cleavage of these latter groups requires drastic acid conditions such as the use of hydrogen bromide, hydrogen fluoride, or boron trifluoroacetate in trifluoroacetic acid. Of course, any of the more labile groups will also be cleaved under the stronger acid conditions. Appropriate selection of the amino protecting groups thus will include the use of a group at the α-amino function which is more labile than that employed as the ε-amino protecting group coupled with cleavage conditions designed to selectively remove only the α-amino function. In this context, $R_2$ preferably is o-chlorobenzyloxycarbonyl or cyclopentyloxycarbonyl, and, in conjunction therewith, the α-amino protecting group of choice for use in each of the amino acids which is added to the peptide chain preferably is t-butyloxycarbonyl.

The groups $R_3$ and $R_4$ represent the hydroxyl hydrogen or a protecting group for the alcoholic hydroxyl of threonine and serine, respectively. Many such protecting groups are described in McOmie, supra, Chapter 3, authored by C. B. Reese. Typical such protecting groups are, for example, $C_1-C_4$ alkyl, such as methyl, ethyl, t-butyl, and the like; benzyl; substituted benzyl, such as p-methoxybenzyl, p-nitrobenzyl, p-chlorobenzyl, o-chlorobenzyl, and the like; $C_1-C_3$ alkanoyl, such as formyl, acetyl, and propionyl; triphenylmethyl (trityl); and the like. Preferably, when $R_3$ and $R_4$ are protecting groups, the protecting group of choice in both instances is benzyl.

The group $R_5$ represents either hydrogen or formyl and defines the moiety $>NR_5$ of the tryptophan residue. The formyl serves as a protecting group. The use of such a protecting group is optional and, therefore, $R_5$ properly can be hydrogen (N-unprotected) or formyl (N-protected).

The group X relates to the carboxyl terminal of the tetradecapeptide chain; it can be hydroxyl, in which case a free carboxyl group is defined. In addition, X represents the solid resin support to which the carboxyl terminal moiety of the peptide is linked during its synthesis. This solid resin is represented by the formula

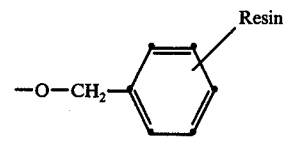

In any of the above, when X represents hydroxyl, each of R, $R_1$, $R_2$, $R_3$, $R_4$, and $R_5$ is hydrogen. When X represents the solid resin support, each of R, $R_1$, $R_2$, $R_3$, and $R_4$ is a protecting group.

The following abreviations, most of which are well known and commonly used in the art, are employed herein:
Ala — Alanine
Asn — Asparagine
Cys — Cysteine
Gly — Glycine
Lys — Lysine
Phe — Phenylalanine
Ser — Serine
Thr — Threonine
Trp — Tryptophan Val — Valine
DCC — N,N'-Dicyclohexylcarbodiimide
DMF — N,N-Dimethylformamide
BOC — t-Butyloxycarbonyl
PMB — p-Methoxybenzyl
CBzOC — o-Chlorobenzyloxycarbonyl
CPOC — Cyclopentyloxycarbonyl
Bzl — Benzyl
For — Formyl
BpOC — 2-(p-biphenyl)isopropyloxycarbonyl Although the selection of the particular protecting groups to be employed in preparing the compounds of this invention remains a matter well within the ordinary skill of a synthetic peptide chemist, it is well to recognize that the sequence of reactions which must be carried out gives rise to a selection of particular protecting group. In other words, the protecting group of choice must be one which is stable both to the reagents and under the conditions employed in the succeeding steps of the reaction sequence. For example, as already discussed to some degree hereinabove, the particular protecting group which is employed must be one which remains intact under the conditions which are employed for cleaving the α-amino protecting group of the terminal amino acid residue of the peptide fragment in preparation for the coupling of the next succeeding amino acid fragment to the peptide chain. It is also important to select, as a protecting group, one which will remain intact during the building of the peptide chain and which will be readily removable upon completion of the synthesis of the desired tetradecapeptide product. All of these matters are well within the knowledge and understanding of a peptide chemist of ordinary skill in the art.

As is evident from the above discussion, the tetradecapeptides of this invention can be prepared by solid phase synthesis. This synthesis involves a sequential building of the peptide chain beginning at the C-terminal end of the peptide. Specifically, cysteine first is linked at its carboxyl function to the resin by reaction of an amino-protected, S-protected cysteine with a chloromethylated resin or a hydroxymethyl resin. Preparation of a hydroxymethyl resin is described by Bodanszky et al., Chem. Ind. (London), 38 1597-98 (1966). The chloromethylated resin is commercially available from Lab Systems, Inc., San Mateo, Calif.

In accomplishing linkage of the C-terminal cysteine to the resin, the protected cysteine first is converted to its cesium salt. This salt then is reacted with the resin in accordance with the method described by B. F. Gisin, Helv. Chim., Acta, 56, 1476 (1973). Alternatively, the cysteine can be linked to the resin by activation of the carboxyl function of the cysteine molecule by application of readily recognized techniques. For example, the cysteine can be reacted with the resin in the presence of a carboxyl group activating compound such as N,N'-dicyclohexylcarbodiimide (DCC).

Once the free carboxyl cysteine has been appropriately linked to the resin support, the remainder of the peptide building sequence involves the step-wise addition of each amino acid to the N-terminal portion of the peptide chain. Necessarily, therefore, the particular sequence which is involved comprises a cleavage of the α-amino protecting group from the amino acid which represents the N-terminal portion of the peptide fragment followed by coupling of the next succeeding amino acid residue to the now free and reactive N-terminal amino acid. Cleavage of the α-amino protecting group can be effected in the presence of an acid such as hydrobromic acid, hydrochloric acid, trifluoroacetic acid, p-toluenesulfonic acid, benzenesulfonic acid, naphthalenesulfonic acid, acetic acid, and the like, with formation of the respective acid addition salt product. Another method which is available for accomplishing cleavage of the amino protecting group involves the use of boron trifluoride. For example, boron trifluoride diethyl etherate in glacial acetic acid will convert the amino-protected peptide fragment to a $BF_3$ complex which then can be converted to the deblocked peptide fragment by treatment with a base such as aqueous potassium bicarbonate. Any of these methods can be employed as long as it is recognized that the method of choice must be one which accomplishes cleavage of the N-terminal α-amino protecting group without disruption of any other protecting groups present on the peptide chain. In this regard, it is preferred that the cleavage of the N-terminal protecting group be accomplished using trifluoroacetic acid. Generally, the cleavage will be carried out at a temperature from about 0° C. to about room temperature.

Once the N-terminal cleavage has been effected, the product which results normally will be in the form of the acid addition salt of the acid which has been employed to accomplish the cleavage of the protecting group. The product then can be converted to the free terminal amino compound by treatment with a mild base, typically a tertiary amine such as pyridine, triethylamine, or the like.

The peptide chain then is ready for reaction with the next succeeding amino acid. This can be accomplished by employing any of several recognized techniques. In order to achieve coupling of the next-succeeding amino acid to the N-terminal peptide chain, an amino acid which has a free carboxyl but which is suitably protected at the α-amino function as well as at any other active moiety is employed. The amino acid then is subjected to conditions which will render the carboxyl function active to the coupling reaction. One such activation technique which can be employed in the synthesis involves the conversion of the amino acid to a mixed anhydride. Thereby, the free carboxyl function of the amino acid is activated by reaction with another acid, typically a carbonic acid in the form of its acid chloride. Examples of such acid chlorides which can be used to form the appropriate mixed anhydrides are ethyl chloroformate, phenyl chloroformate, sec-butyl chloroformate, isobutyl chloroformate, pivaloyl chloride, and the like.

Another method of activating the carboxyl function of the amino acid to achieve coupling is by conversion of the amino acid to its active ester derivative. Examples of such active esters are, for example, a 2,4,5-trichlorophenyl ester, a pentachlorophenyl ester, a p-nitrophenyl ester, an ester formed from 1-hydroxybenzotriazole, and an ester formed from N-hydroxysuccinimide. Another method for effecting coupling of the C-terminal amino acid to the peptide fragment involves carrying out the coupling reaction in the presence of at least an equimolar quantity of N,N'-dicyclohexylcarbodiimide (DCC). This latter method is preferred for preparing the tetradecapeptide of this invention.

Once the desired amino acid sequence has been prepared, the resulting peptide can be removed from the resin support. This is accomplished by treatment of the protected resin-supported tetradecapeptide with hydrogen fluoride. Treatment with hydrogen fluoride cleaves the peptide from the resin; in addition, however, it cleaves all remaining protecting groups present on the reactive moieties located on the peptide chain as well as the α-amino protecting group present at N-terminal amino acid. When hydrogen fluoride is employed to effect the cleavage of the peptide from the resin as well as to remove the protecting groups, it is preferred that the reaction be carried out in the presence of anisole. The presence of anisole has been found to inhibit the potential alkylation of certain amino acid residues present in the peptide chain. In addition, it is preferred that the cleavage be carried out in the presence of ethyl mercaptan. The ethyl mercaptan serves to protect the indole ring of the tryptophan residue, and, furthermore, it facilitates conversion of the blocked cysteines to their thiol forms. Also, when $R_5$ is formyl, the presence of ethyl mercaptan facilitates hydrogen fluoride cleavage of the formyl group.

Once the cleavage reaction has been accomplished, the product which is obtained is a straight-chain peptide containing 14 amino acid residues. In order to obtain the final product of this invention, it is necessary to treat the straight-chain tetradecapeptide under conditions which will effect its oxidation by converting the two sulfhydryl groups present in the molecule, one at each cysteinyl moiety, to a disulfide bridge. This can be accomplished by treating a dilute solution of the linear tetradecapeptide with any of a variety of oxidizing agents including, for example, iodine, potassium ferricyanide, and the like. Air also can be employed as oxidizing agent, the pH of the mixture generally being from about 2.5 to about 9.0, and preferably from about 7.0 to about 7.6. When air is used as oxidizing agent, the concentration of the peptide solution generally is not greater than about 0.4 mg. of the peptide per milliliter of solution, and usually is about 50 μg./ml.

The compounds of this invention having the disulfide linkage may be administered to warm-blooded mammals, including humans, by any of several methods, including orally, sublingually, subcutaneously, intramuscularly, intravenously, and the like. Each of these compounds is active, although not necessarily to an equivalent degree, in inhibiting the release of growth hormone. This inhibitory effect is beneficial in those instances in which the host being treated requires a therapeutic treatment for excess secretion of somatotropin, such secretion being associated with adverse conditions such as juvenile diabetes and acromegaly. These compounds also exhibit other physiological effects, including the inhibition of gastric acid secretion, useful in treatment of ulcer conditions; the inhibition of exocrine pancreas secretion, potentially useful in treatment of pancreatitis; the inhibition of secretion of insulin and glucagon; and the reduction of gut motility, useful in gastrointestinal radiology. Preferably, the dose range for sublingual or oral administration is about 1 mg. to about 100 mg./kg. of body weight per day. Generally, the dose range for intravenous, subcutaneous, or intramuscular administration is from about 10 μg. to about 1 mg./kg. of body weight per day, and, preferably, is from about 50 μg. to about 100 μg./kg. of body weight per day. It is evident that the dose range will vary widely depending upon the particular condition which is being treated as well as the severity of the condition.

It is also possible to administer the compounds of this invention in association with a pharmaceutical carrier, for example, in the form of tablets or capsules. Inert diluents or carriers, for example, magnesium carbonate or lactose, can be used together with conventional disintegrating agents, for example, maize starch and alginic acid, and lubricating agents, for example, magnesium stearate. Typically, the amount of carrier or diluent will range from about 5 to about 95 percent of the final composition, and preferably from about 50 to about 85 percent of the final composition. Suitable flavoring agents also can be employed in the final preparation rendering the composition more palatable for administration.

When the compounds of this invention are to be administered intravenously, suitable carriers may be employed, such as, for example, isotonic saline, phosphate buffer solutions, and the like.

The following examples are illustrative of the preparation of compounds of this invention.

EXAMPLE 1

N-t-BUTYLOXYCARBONYL-L-CYSTEINYL(S-p-METHOXYBENZYL) METHYLATED POLYSTYRENE RESIN

To 500 ml. of N,N-dimethylformamide (DMF) containing the cesium salt of N-t-butyloxycarbonyl-(S-p-methoxybenzyl)-cysteine [prepared from 9.06 g. (26.5 mmoles) of the free acid] were added 51.0 g. of chloromethylated polystyrene resin (Lab Systems, Inc., 0.75 mmoles/gram). The mixture was stirred at room temperature for 6 days. The resin then was filtered and was washed successively 3 times with a mixture of 90 percent DMF and 10 percent water, three times with 95% ethanol, and three times with DMF. To the resin suspended in 500 ml. of DMF were added a solution of 10.5 grams of cesium acetate. The mixture was stirred for six days at room temperature. The resin then was filtered and was washed successively, once with aqueous DMF, three times with a mixture of 90 percent DMF and 10 percent water, three times with 95% ethanol, three times with methylene chloride, three times with 95 percent ethanol and three times with chloroform. Fines were removed by suspending the resin in chloroform four times and each time drawing off the liquid. The resin then was dried in vacuo at 40° C. overnight to obtain 44.8 g. of the title product. An amino acid analysis showed 0.25 mmoles of Cys per gram resin. The cysteine was determined as cysteic acid from an acid hydrolysis carried out using a 1:1 mixture of dioxane and conc. hydrochloric acid to which a small amount of dimethyl sulfoxide was added.

EXAMPLE 2

N-t-BUTYLOXYCARBONYL-D-VALYL-GLYCYL-L-(S-p-METHOXY-BENZYL)CYSTEINYL-L-(N$^\epsilon$-o-CHLOROBENZYLOXYCARBONYL)-LYSYL-L-ASPARAGINYL-L-PHENYLALANYL-L-PHENYLALANYL-L-(FORMYL)TRYPTOPHYL-L-(N$^\epsilon$-o-CHLOROBENZYLOXYCARBONYL) LYSYL-L-(O-BENZYL)THREONYL-L-PHENYLALANYL-L-(O-BENZYL) THREONYL-L-(O-BENZYL)SERYL-L-(S-p-METHOXYBENZYL)CYSTEINYL METHYLATED POLYSTYRENE RESIN The product from Example 1 (7.0 grams) was placed in the reaction vessel of a Beckman 990 automatic peptide synthesizer, and 12 of the remaining 13 amino acids were added employing the automatic synthesizer. The resulting protected tridecapeptide resin was divided into two equal portions, and the final residue was introduced to one of the portions. The amino acids which were employed as well as the sequence of their employment is as follows: (1) N-t-butyloxycarbonyl-(O-benzyl)-L-serine; (2) N-t-butyloxy-carbonyl-(O-benzyl)-L-threonine; (3) N-t-butyloxycarbonyl-L-phenylalanine; (4) N-t-butyloxycarbonyl-(O-benzyl)-L-threonine; (5) $N^\alpha$-t-butyloxycarbonyl-$N^\epsilon$-o-chlorobenzyl-oxycarbonyl-L-lysine; (6) $N^\alpha$-t-butyloxycarbonyl-(N-formyl)-L-tryptophan; (7) N-t-butyloxycarbonyl-L-phenylalanine; (8) N-t-butyloxycarbonyl-L-phenylalanine; (9) N-t-butyloxy-carbonyl-L-asparagine, p-nitrophenyl ester; (10) $N^\alpha$-t-butyloxycarbonyl-$N^\epsilon$-o-chlorobenzyloxycarbonyl-L-lysine; (11) N-t-butyloxycarbonyl-(S-p-methoxybenzyl)-L-cysteine; (12) N-t-butyloxycarbonyl-glycine; and (13) N-t-butyloxycarbonyl-D-valine. The sequence of deprotection, neutralization, coupling, and recoupling for the introduction of each amino acid into the peptide is as follows: (1) three washes (10 ml./gram resin) of three minutes each with chloroform; (2) removal of BOC group by treatment twice for twenty minutes each with 10 ml./gram resin of a mixture of 29 percent trifluoroacetic acid, 48 percent chloroform, 6 percent triethylsilane, and 17 percent methylene chloride; (3) two washes (10 ml./gram resin) of three minutes each with chloroform; (4) one wash (10 ml./gram resin) of three minutes with methylene chloride; (5) three washes (10 ml./gram resin) of three minutes each with a mixture of 90 percent t-butyl alcohol and 10 percent t-amyl alcohol; (6) three washes (10 ml./gram resin) of 3 minutes each with methylene chloride; (7) neutralization by three treatments of three minutes each with 10 ml./gram resin of 3 percent triethylamine in methylene chloride; (8) three washes (10 ml./gram resin) of three minutes each with methylene chloride; (9) three washes (10 ml./gram resin) of three minutes each with a mixture of 90 percent t-butyl alcohol and 10 percent t-amyl alcohol; (10) three washes (10 ml./gram resin) of three minutes each with methylene chloride; (11) addition of 1.0 mmole/gram resin of the protected amino acid and 1.0 mmole/gram resin of N,N'-dicyclohexylcarbodiimide (DCC) in 10 ml./gram resin of methylene chloride followed by mixing for 120 minutes; (12) three washes (10 ml./gram resin) of three minutes each with methylene chloride; (13) three washes (10 ml./gram resin) of three minutes each with a mixture of 90 percent t-butyl alcohol and 10 percent t-amyl alcohol; (14) three washes (10 ml./gram resin) of three minutes each with methylene chloride; (15) neutralization by three treatments of three minutes each with 10 ml./gram resin of 3 percent triethylamine in methylene chloride; (16) three washes (10 ml./gram resin) of three minutes each with methylene chloride; (17) three washes (10 ml./gram resin) of three minutes each with a mixture of 90 percent t-butyl alcohol and 10 percent t-amyl alcohol; (18) three washes (10 ml./gram resin) of three minutes each with methylene chloride; (19) three washes (10 ml./gram resin) of three minutes each with DMF; (20) addition of 1.0 mmole/gram resin of the protected amino acid and 1.0 mmole/gram resin of N,N'-dicyclohexylcarbodiimide (DCC) in 10 ml./gram resin of a 1:1 mixture of DMF and methylene chloride followed by mixing for 120 minutes; (21) three washes (10 ml./gram resin) of 3 minutes each with DMF; (22) three washes (10ml./gram resin) of three minutes each with methylene chloride; (23) three washes (10 ml./gram resin) of three minutes each with a mixture of 90 percent t-butyl alcohol and 10 percent t-amyl alcohol; (24) three washes (10 ml./gram resin) of three minutes each with methylene chloride; (25) neutralization by three treatments of three minutes each with 10 ml./gram resin of 3 percent triethylamine in methylene chloride; (26) three washes (10 ml./gram resin) of three minutes each with methylene chloride; (27) three washes (10 ml./gram resin) of three minutes each with a mixture of 90 percent t-butyl alcohol and 10 percent t-amyl alcohol; and (28) three washes (10 ml./gram resin) of three minutes each with methylene chloride.

The above treatment sequence was employed for addition of each of the amino acids with the exception of the glycine and the asparagine residues. Addition of the glycine residue employed only Steps 1-18. The asparagine residue was incorporated via its p-nitrophenyl active ester. In doing so, Step (11) above was modified to the following 3-step sequence: (a) three washes (10 ml./gram resin) of three minutes each with DMF; (b) addition of 1.0 mmole/gram resin of the p-nitrophenyl ester of N-t-butyloxycarbonyl-L-asparagine in 10 ml./gram resin of a 1:3 mixture of DMF and methylene chloride followed by mixing for 720 minutes; and (c) three washes (10 ml./gram resin) of three minutes each with DMF. Also, Step (20) above was modified to the use of the p-nitrophenyl ester of N-t-butyloxycarbonyl-L-asparagine in a 3:1 mixture of DMF and methylene chloride followed by mixing for 720 minutes.

The finished peptide-resin was dried in vacuo. A portion of the product was hydrolyzed by refluxing for 72 hours in a mixture of hydrochloric acid and dioxane. Amino acid analysis of the resulting product gave the following results, lysine being employed as standard: Asn, 1.04; 2Thr, 2.68; Ser, 1.08; Val, 1.12; Gly, 1.04; 3Phe, 3.87; 2Lys, 2.00, Trp, 0.75.

Tryptophan was determined by a 21 hour hydrolysis of a sample of the product in the presence of dimethyl sulfoxide and thioglycolic acid. Cysteine was not determined since it is destroyed by the method of analysis.

EXAMPLE 3

D-VALYL-GLYCYL-L-CYSTEINYL-L-LYSYL-L-ASPARAGINYL-L-PHENYLALANYL-L-PHENYL-ALANYL-L-TRYPTOPHYL-L-LYSYL-L-THREONYL-L-PHENYLALANYL-L-THREONYL-L-SERYL-L-CYSTEINE

To a mixture of 5 ml. of anisole and 5 ml. of ethyl mercaptan were added 2.828 grams (at substitution level of 0.150 mmoles/gram) of the protected tetradecapeptide-resin of Example 2. The mixture was cooled in liquid nitrogen, and 56 ml. of liquid hydrogen fluoride were added by distillation. The resulting mixture was allowed to warm to 0° C. and was stirred for 2 hours. The hydrogen fluoride then was removed by distillation, and ether was added to the remaining mixture. The mixture was cooled to 0° C., and the resulting solid was collected by filtration and washed with ether. The product was dried, and the deprotected tetradecapeptide was extracted from the resin mixture using 1M acetic acid and a small amount of glacial acetic acid. The acetic acid solution then was immediately lyophilized to dryness in the dark. The resulting white solid was suspended in a mixture of 10 ml. of degassed 0.2M acetic acid and 4 ml. of glacial acetic acid. The resulting suspension was heated; however, the solid did not completely dissolve. The insoluble portion was filtered off, and the opaque, colorless filtrate was applied to a Sephadex G-25 F column. The chromatographic conditions were: solvent, degassed 0.2M acetic acid; column size, 7.5 × 150 cm.; temperature, 26° C.; flow rate, 629 ml./hour; fraction volume, 22.0 ml.

Absorbance at 280 mμ of each fraction plotted versus fraction number indicated one large peak with a following shoulder. UV spectroscopy revealed that the main peak was good product. The fractions which were combined and their effluent volumes are as follows:

Fractions 224–240 (4906–5280 ml., peak = 5054 ml.)

This collection of fractions did not include the following shoulder. UV spectroscopy indicated that 175 mg. of the product were present (yield = 24.8%). An Ellman titration of an aliquot indicated a free sulfhydryl content of 93.6% of theoretical.

EXAMPLE 4

OXIDATION TO D-VAL$^1$-SOMATOSTATIN

The solution of the reduced D-Val$^1$-somatostatin (374 ml., theoretically 175 mg.) from Example 3 was diluted with 147 ml. of 0.2M acetic acid and 2967 ml. of distilled water to achieve a concentration of 50 μg./ml. Concentrated ammonium hydroxide was added to adjust the pH of the mixture to 6.7. The solution was stirred at room temperature in the dark for 64 hours after which an Ellman titration indicated that oxidation was complete.

The mixture was concentrated in vacuo to a volume of about 10 ml. The concentrate was diluted with 10 ml. of glacial acetic acid and then was desalted on a Sephadex G-25 F column. The chromatographic conditions were as follows: solvent, degassed 50% acetic acid; column size, 5.0 × 90 cm.; temperature, 26° C.; flow rate, 246 ml./hour; fraction volume, 16.4 ml.

Absorbance at 280 mμ for each fraction plotted versus fraction number indicated two large peaks. The first peak represented the aggregated forms of the product, and the second peak represented monomeric product. The material represented by the second peak [Fractions 49-64 (787-1050 ml.)] was collected and lyophilized to dryness in the dark. The resulting solid was dissolved in 15 ml. of degassed 0.2M acetic acid and was applied to a Sephadex G-25 F column. Chromatographic conditions were: solvent, degassed 0.2M acetic acid; column size, 5.0 × 150 cm.; temperature, 26° C.; flow rate, 475 ml./hour; fraction volume, 16.6 ml.

Absorbance at 280 mμ for each fraction plotted versus fraction number showed one large peak. UV spectroscopy indicated that the main part of the peak was good product. Fractions 157–172 (effluent volumes of 2590–2855 ml., peak = 2667 ml.) were combined and lyophilized to dryness in the dark. UV spectroscopy indicated 95 mg. of the desired product (yield from reduced form = 54.3%).

A portion of the resulting solid was dissolved in 5 ml. of 50% acetic acid and was rechromatographed on a Sephadex G-25 F column. The chromatographic conditions were: solvent, degassed 50% acetic acid; column size, 2.5 × 180 cm.; temperature, 26° C.; flow rate, 53.2 ml./hour; fraction volume, 8.87 ml.

Absorbance at 280 mμ of each fraction plotted versus fraction number indicated one large peak. UV spectroscopy indicated that the major portion of the peak was good product. Fractions 56–60 (488–532 ml., peak = 505 ml.) were combined and lyophilized to dryness in the dark.

Optical rotation $[\alpha]_D^{26} = -42.1°$ (1 percent acetic acid).

Amino acid analysis: Val, 0.98; Gly, 1.01; 2Cys, 1.81; 2Lys, 1.99; Asn, 0.95; 3Phe, 2.94; Trp, 0.80; 2Thr, 1.91; Ser, 0.85.

The above results are expressed as ratios to (Gly + Lys)/3 = 1.0. The following three 21 hour hydrolyses were run:

(1) In presence of dimethyl sulfoxide to oxidize cysteine to cysteic acid.
(2) Thioglycolic acid scavenged.
(3) Without scavenger or oxidizer.

All of the above values are averages of the three hydrolyses except the following:

Cys and Ser; (1) and (3) only;
Trp; (2) only;
Phe; (2) and (3) only.

D-Val$^1$-somatostatin was tested in dogs for its in vivo inhibition of gastric acid secretion. In six dogs with chronic fistula and Heidenhain pouch, gastric HCl secretion was induced by infusion of the C-terminal tetrapeptide of gastrin at 0.5 μg/kg-hr. Each dog served as its own control, receiving on a separate day only the tetrapeptide. On another day, the six dogs received the tetrapeptide, and, after one hour of steady state secretion of HCl, D-Val$^1$-somatostatin was infused at 0.75 μg/kg-hr. for one hour. Collection of gastric acid samples was continued for an additional 1.5 hours at 15 minute intervals. The samples were titrated to pH 7 with an automatic titrator. The maximal inhibitory effect of the D-Val$^1$-somatostatin was extrapolated against the dose-response curve of somatostatin, and the relative potency of the analog to that of somatostatin is expressed as percent activity. D-Val$^1$-somatostatin inhibited steady state acid secretion induced by the C-terminal tetrapeptide of gastrin by 85.1 ± 6.0% standard error of mean. This effect is equivalent to that of 0.935 μg/kg-hr. of somatostatin. Its activity relative to that of somatostatin thus is 125%.

D-Val$^1$-somatostatin also was tested for its action on gut motility in conscious dogs. Three dogs having intralumenal catheters placed in the antrum, duodenum, and pylorus were used. Pressure changes in the gut lumen were recorded on a Visicorder using strain gauges and miniature light beam galvanometers. After a steady state control was established, D-Val$^1$-somatostatin was infused intravenously over a ten minute period. The compound initially increased the intralumenal pressure in the pylorus and then decreased it whereas the pressure in the duodenum and the antrum remained depressed throughout the test. The minimum effective dose required to increase the pyloric pressure and to decrease the duodenum and antrum pressures was <0.125 μg./kg.-10 minutes. This compares to an activity for somatostatin itself of 0.125 to 0.25 μg./kg.-10 minutes.

D-Val$^1$-somatostatin also was shown to inhibit pancreatic secretion. In three dogs having both pancreatic and total gastric fistula, secretion from the pancreas was induced by infusion of secretin at 2 units/kg-hr. and cholecystokinin at 0.45 unit/kg-hr., and secretion of gastric HCl by infusion of tetragastrin at 0.5 μg/kg-hr. After a steady response was established, each dog received D-Val$^1$-somatostatin for one hour at 0.75 μg/kg-hr. The peak inhibitory effect expressed as percent change over control for total protein was −51%

D-Val$^1$-somatostatin also was tested for its activity with respect to the release of growth hormone. The procedure which was employed is carried out using normal male SpragueDawley rats weighing 100-120 grams (Laboratory Supply Company, Indianapolis, Indiana). The test is a modification of the method of P. Brazeau, W. Vale, and R. Guilleman, Endocrinology, 94 184 (1974). In this assay, five groups of eight rats each were employed. Sodium pentobarbital was administered intraperitoneally to all of the rats to stimulate growth hormone secretion. One group served as the control and received only saline. Two of the groups received somatostatin, one at 2 μg./rat, subcutaneously, and the other at 50 μg./rat, subcutaneously. The other two groups received D-Val¹-somatostatin, one at 2 μg./rat, subcutaneously, and the other at 50 μg./rat, subcutaneously. The serum concentration of growth hormone was measured 20 minutes after simultaneous administration of sodium pentobarbital and test compound. The degree of inhibition of serum growth hormone concentration then was determined with respect to the control group, and the relative activities of D-Val¹-somatostatin and somatostatin itself were compared.

At a dose level of 2 μg./rat, D-Val¹-somatostatin inhibited the increase in growth hormone secretion by 2% over control while somatostatin produced a 44% inhibition. At a dose level of 50 μg./rat, D-Val¹-somatostatin inhibited the increase in growth hormone secretion by 73% over control, while somatostatin itself produced a 79% inhibition.

D-Val¹-somatostatin was tested for its in vivo activity in inhibiting glucagon and insulin secretion upon stimulation with L-alanine. Normal mongrel dogs of either sex were fasted overnight. Control blood samples were obtained, and then an intravenous infusion of saline, somatostatin, or D-Val¹-somatostatin was started. After 30 minutes, L-alanine additionally was administered intravenously for a period of 15 minutes. The infusion of saline, somatostatin, or D-Val¹-somatostatin was continued for 15 minutes after completion of the L-alanine infusion. The infusion of L-alanine caused an abrupt increase in serum concentration of glucagon and insulin which returned to control concentration upon termination of the L-alanine infusion. From the above it was determined that the minimal dose of D-Val¹-somatostatin for the inhibition of glucagon is 0.06 to 0.11 μg./kg./min. and for the inhibition of insulin is 0.006 to 0.03 μg./kg./min., whereas the minimal dose of somatostatin for the inhibition of glucagon is 0.10 to 0.12 μg./kg./min. and for the inhibition of insulin is 0.03 to 0.10 μg./kg./min.

I claim:

1. A compound selected from those of the formula

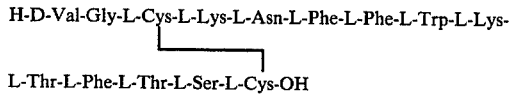

and its pharmaceutically acceptable non-toxic acid addition salts, and intermediates to said compounds, said intermediates having the formula R-D-Val-Gly-L-Cys(R₁)-L-Lys(R₂)-L-Asn-L-Phe-L-Phe-L-Trp(R₅)-L-Lys(R₂)-L-Thr(R₃)-L-Phe-L-Thr(R₃)-L-Ser(R₄)-L-Cys(R₁)-X; in which R is hydrogen or an α-amino protecting group;
R₁ is hydrogen or a thio protecting group;
R₂ is hydrogen or an ε-amino protecting group;
R₃ and R₄ each are hydrogen or a hydroxy protecting group;
R₅ is hydrogen or formyl; and
X is hydroxy or

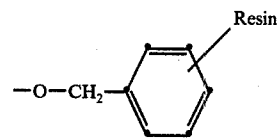

in which the resin is polystyrene; with the proviso that, when X is hydroxy, each of R, R₁, R₂, R₃, R₄, and R₅ is hydrogen, and, when X is

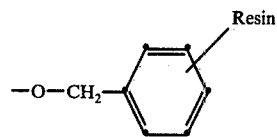

each of R, R₁, R₂, R₃, and R₄ is other than hydrogen.

2. Compound of claim 1, having the formula

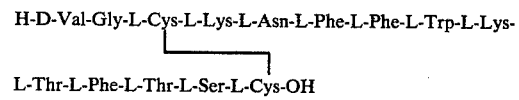

and pharmaceutically acceptable non-toxic acid addition salts thereof.

3. Compound of claim 1, having the formula R-D-Val-Gly-L-Cys(R₁)-L-Lys(R₂)-L-Asn-L-Phe-L-Phe-L-Trp(R₅)-L-Lys(R₂)-L-Thr(R₃)-L-Phe-L-Thr(R₃)-L-Ser(R₄)-L-Cys(R₁)-X.

4. Compound of claim 3, in which X is hydroxy.

5. Compound of claim 3, in which X is

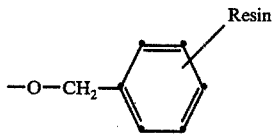

6. Compound of claim 5, in which R is t-butyloxycarbonyl.

7. Compound of claim 5, in which R₁ is p-methoxybenzyl.

8. Compound of claim 5, in which R₂ is o-chloro-benzyloxycarbonyl.

9. Compound of claim 5, in which R₃ and R₄ are benzyl.

10. Compound of claim 5, having the formula

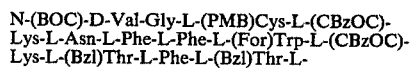
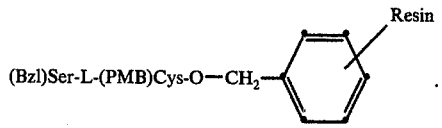

UNITED STATES PATENT AND TRADEMARK OFFICE
CERTIFICATE OF CORRECTION

PATENT NO. : 4,100,117
DATED : July 11, 1978
INVENTOR(S) : James E. Shields

It is certified that error appears in the above-identified patent and that said Letters Patent are hereby corrected as shown below:

Title page, Abstract, formula, should read:

D-Val-Gly-L-Cys-L-Lys-L-Asn-L-Phe-

L-Phe-L-Trp-L-Lys-L-Thr-L-Phe-L-Thr-L-Ser-L-Cys-OH

Column 1, line 9, formula, should read:

D-Val-Gly-L-Cys-L-Lys-L-Asn-L-Phe-

L-Phe-L-Trp-L-Lys-L-Thr-L-Phe-L-Thr-L-Ser-L-Cys-OH

Signed and Sealed this

Eighth Day of May 1979

[SEAL]

Attest:

RUTH C. MASON
Attesting Officer

DONALD W. BANNER
Commissioner of Patents and Trademarks